United States Patent [19]

Sibalis

[11] Patent Number: 5,605,536
[45] Date of Patent: *Feb. 25, 1997

[54] TRANSDERMAL DRUG APPLICATOR AND ELECTRODES THEREFOR

[75] Inventor: Dan Sibalis, Stony Brook, N.Y.

[73] Assignee: Drug Delivery Systems Inc., New York, N.Y.

[ * ] Notice: The term of this patent shall not extend beyond the expiration date of Pat. No. 4,640,689.

[21] Appl. No.: 136,726

[22] Filed: Oct. 14, 1993

Related U.S. Application Data

[63] Continuation of Ser. No. 858,544, Mar. 27, 1992, abandoned, which is a continuation of Ser. No. 746,691, Aug. 16, 1991, abandoned, which is a division of Ser. No. 428,478, Oct. 30, 1989, Pat. No. 5,087,240, which is a division of Ser. No. 198,652, May 25, 1988, abandoned, which is a continuation of Ser. No. 922,296, Oct. 23, 1986, abandoned, which is a division of Ser. No. 839,050, Mar. 12, 1986, Pat. No. 4,640,689, which is a continuation of Ser. No. 702,486, Feb. 19, 1985, abandoned, which is a continuation-in-part of PCT/US85/00080, Jan. 3, 1990, which is a continuation-in-part of Ser. No. 660,192, Oct. 12, 1984, Pat. No. 4,622,031, which is a continuation-in-part of Ser. No. 524,252, Aug. 18, 1983, Pat. No. 4,557,723.

[51] Int. Cl.$^6$ ............................................. A61N 1/30
[52] U.S. Cl. ................................... 604/20; 607/149
[58] Field of Search ............................. 604/20; 607/152, 607/153, 149

[56] References Cited

U.S. PATENT DOCUMENTS

| | | | |
|---|---|---|---|
| 2,047,308 | 7/1936 | Chapman | 128/798 |
| 4,200,104 | 4/1980 | Harris | 607/153 |
| 4,325,367 | 4/1982 | Tapper | 604/20 |
| 4,457,748 | 7/1984 | Lattin et al. | 604/20 |
| 4,460,370 | 7/1984 | Allison et al. | 604/93 |
| 4,640,689 | 2/1987 | Sibalis | 604/20 |
| 4,865,582 | 9/1989 | Sibalis | 604/20 |
| 4,883,457 | 11/1989 | Sibalis | 604/20 |
| 4,919,648 | 4/1990 | Sibalis | 604/20 |
| 4,921,475 | 5/1990 | Sibalis | 604/20 |
| 5,087,240 | 2/1992 | Sibalis | 604/20 |

*Primary Examiner*—Randall L. Green
*Assistant Examiner*—Mark Bockelman
*Attorney, Agent, or Firm*—Lackenbach Siegel Marzullo Aronson & Greenspan, P.C.

[57] ABSTRACT

An improved transdermal drug applicator for application to a living body for the migration of at least one medicament through the skin into the blood stream embodying at least two electrode elements forming the applicator and with the electrodes separated from each other by insulating means. A reservoir means, in at least one of said electrode elements of said applicator, containing said medicament; and a circuit, including a power source, for supplying electric power to said electrodes and such reservoir means. Suitable cover means partially enclosed at least said reservoir means, and adhesive means affixes the applicator to the skin, so as to complete an electrical circuit through the skin when the applicator is affixed thereto, thus creating at least one physico/chemical mass transfer phenomenon which causes said medicament to migrate through the skin.

14 Claims, 4 Drawing Sheets

TRANSDERMAL DRUG APPLICATOR AND ELECTRODES THEREFOR

This application is a continuation of U.S. patent application Ser. No. 07/858,544 filed on Mar. 27, 1992 now abandoned; which is a continuation of U.S. patent application Ser. No. 07/746,691 filed on Aug. 16, 1991 now abandoned; which is a division of U.S. patent application Ser. No. 07/428,478 filed on Oct. 30, 1989 now U.S. Pat. No. 5,087,240; which is a division of U.S. patent application Ser. No. 07/198,652 filed on May 25, 1988 now abandoned; which is a continuation of U.S. patent application Ser. No. 06/922,296 filed on Oct. 23, 1986 now abandoned; which is a division of U.S. patent application Ser. No. 06/839,050 filed on Mar. 12, 1986 now U.S. Pat. No. 4,640,689; which is a which is a continuation U.S. patent application Ser. No. 06/702,486 filed Feb. 19, 1985 now abandoned; which is a is continuation-in-part of Pct 01/000,080 and a continuation-in-part of U.S. patent application Ser. No. 06/660,192 filed on Oct. 12, 1984 now U.S. Pat. No. 4,622,031; the later of which is a continuation-in-part of U.S. patent application Ser. No. 06/524,252 filed on Aug. 18, 1983 now U.S. Pat. No. 4,557,723.

FIELD OF THE INVENTION

This invention relates to transdermal drug applicators, as well as to electrode constructions for use with such applicators; and more particularly to drug applicators which are electrically operated and exhibit a mass transfer phenomena which facilitates the transcutaneous delivery or transfer of drugs, medicaments, and the like.

SUMMARY OF THE INVENTION

Transdermal drug applicators embody various electrode constructions. However, since the overall size of the applicator should be minimized for cost effectiveness and aesthetics and the dosage capability desirably maximized, it is an object of the present invention to provide improved applicators as well as improved electrode constructions which are applicable to both the active and inactive electrodes. In addition, it is another object of the invention to provide drug applicators which employ only active electrodes, or with different drugs in each electrode structure, or with the active and inactive electrodes of different sizes. Moreover, the invention further pertains to drug applicators incorporating three electrodes which may operate to deliver drugs independently of each other using separate mass transfer phenomenas, such as electrophoresis and electroosmosis or endosmose.

These and other objects and advantages of the invention will become more apparent from a reading of the following detailed description of the preferred modifications and embodiments of the invention.

DESCRIPTION OF THE PREFERRED EMBODIMENTS

Figure 1:
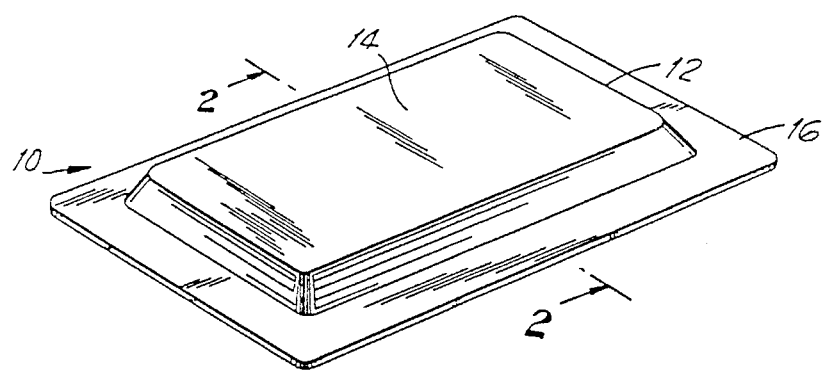
FIG. 1 is a perspective view taken from above or the top of a drug applicator embodying the principles of the invention.
Figure 2:
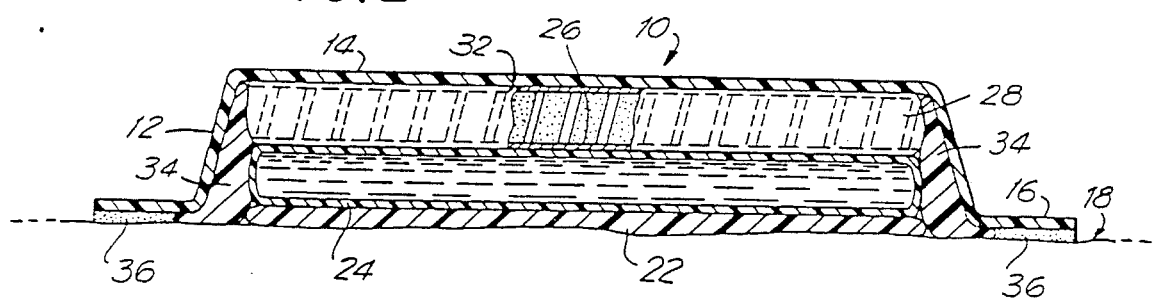
FIG. 2 is a cross-sectional view taken along the line 2—2 of FIG. 1 and showing the applicator mounted on skin.

Referring to FIGS. 1 and 2, applicator 10 consists of an outer cover 12 having a raised portion 14 and a lip 16 along the outer periphery. It is understood that applicator 10 can have any convenient shape or size, for example, square, rectangular, oval, circular, or tailored for a specific location on the skin, as long as this is a raised central portion to accommodate the rest of the electrophoresis unit to be described and the lip along its periphery.

As seen in FIG. 2, where applicator 10 is mounted on the surface of skin 18 of a patient, enclosed within the raised portion 14 of cover 12 are several layers to be described. The first layer is a microporous or semi-permeable membrane 22 through which the medicament migrates to be deposited on skin 18. As will be noted from the following discussion, membrane 22 may not be needed depending on the nature of the reservoir for the medicament.

The second layer consists of a flexible pouch or reservoir 24 containing the drug to be administered. As is understood in the art, and shown in one or more of the U.S. patents identified above, reservoir 24 can be a pouch containing the drug of choice in solution or suspension, the walls of which are sufficiently dense to prevent leakage of the drug under ambient conditions, but sufficiently porous to permit migration of the charged particles or ions under the influence of the electric field imposed. It should be noted that it would be appropriate to employ the microporous membrane 22 when leakage under ambient conditions could occur, for example, as a result of packing of the applicators for shipment or storage, fluctuating temperatures, and possibly puncture of the reservoir. Also, the use of the membrane 22 could depend in large measure on the nature of the medicament involved. In the alternative, reservoir 24 can consist of porous material in which the drug is impregnated rather than a pouch containing the liquid medicament.

The third or next layer above reservoir 24 is an extended contact 26 which could be incorporated as one face of battery 28 which is the next layer. Contact 26 could be any suitable conductive material, preferably conformable to permit applicator 10 to be curved or bent to conform to the shaped surface of the skin. Suitable materials of this type are well known in the art and include electrically conductive polymers, preferable non-ionic. Carbon loaded or surface metalized plastics are also available for such use.

Battery 28 comprising the next layer can be made up of a group of cells internally connected in series to obtain the desired voltage necessary to obtain the electrophoretic action with the particular medicament. Orientation of battery 28 would depend on whether the charged (ionic) particles of the drug of choice are positive or negative. If the particles are negatively charged in solution or suspension then contact 26 would be connected to the negative side of battery 28 as the skin will then be positive with respect to that contact and will attract the ions. With regard to battery 28, it should be noted that any conventional miniaturized battery cells now generally available can be employed, arranged and connected in series to obtain the desired operating voltage. In addition, the technology now exists for batteries which are made up of very thin, flexible sheets of a conductive polymer with high surface areas relative to thickness to provide adequate current densities. One such so-called plastic battery is described in "Batteries Today", Autumn 1981, pages 10, 11, and 24. When such a battery is employed, sheets may be layered to place the cells in series, and an effective compromise between number of sheets and surface areas of sheets is to layer them in a diagonal as shown somewhat schematically in FIG. 2. Of course, battery selection would ultimately depend on such factors as the degree of conformability desired, voltage and current densities required for a specific application, and time of discharge.

Layered above battery 28 would be another contact 32 which could be similar in construction to that of contact 26 and connected electrically to the opposite side of battery 28.

Cover 12 which encloses all of the layers of applicator 10 is made from a flexible conductive plastic material such as a polymer impregnated with carbon or surface metalized plastic. Insulating material 34 fills the space between the side wall of raised portion 14 and the various layers contained therein.

An electrically conductive adhesive material 36 coats the underside of lip 16 so that applicator 10 may be placed on and adhere to skin 18 and make good electrical contact.

It will be seen that the above described arrangement forms a complete electric circuit from one side of battery 28, cover 12, adhesive material 36, skin 18, microporous membrane 22, liquid reservoir 24, and back to battery 28.

Figure 3:
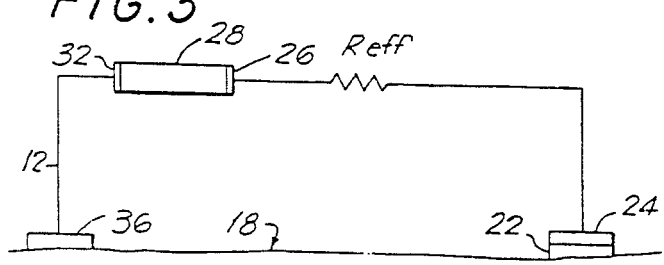
FIG. 3 is an electrical schematic of the circuit incorporated in the drug applicator shown in FIGS. 1–2.

For a more particular description of the electrical circuit formed by the arrangement just described, reference is made to FIG. 3 wherein the circuit is shown schematicaly with numerals corresponding to the structure shown in FIGS. 1 and 2.

Battery 28 is connected through contact 32, cover 12, and adhesive layer 36 to skin 18. The other side of battery 28 is connected electrically through contact 26, liquid reservoir 24 and membrane 22 to skin 18 to complete the circuit. Resistor Reff represents the effective resistance of the complete circuit, including skin 18, the adhesive layer 36, cover 12, battery 28 and its contacts 26 and 32, as well as reservoir 24 and membrane 22, In a system of this type, one of the aims is to establish a very low rate of current flow so that the medicament will be desposited slowly over a long period of time. Current flow of down as low as 0.0001 ampere-hour per square centimeter of skin surface below membrane 22 is a typical current which may be selected for the application of a particular drug. Electrical resistance of the skin to current flow is of the order of 6–9 K ohms and is roughly independent of the distance between the points on the skin where electrical contact is made. This is because skin electrical resistance is largely that of resistance to penetration, the current flowing through the fluids of the body in which electrical resistance being very low. Thus, in order to establish current flow at the rate indicated, by ohm's law, it is seen that total resistance of the circuit using a 1.5 volt battery should be about 360 K ohms for each square centimeter of application. This resistance, the effective resistance, Reff, of the circuit, can be built into any one component or combination of components of the circuit shown in FIG. 3, including the battery resistance, electrodes, cover material, etc. In addition, if desired, in order to maintain current flow constant over the full period of operation a constant current limiting device can be made integral with and a part of conductor 26, or any other part of the circuit where it is found convenient to do so.

Figure 4:
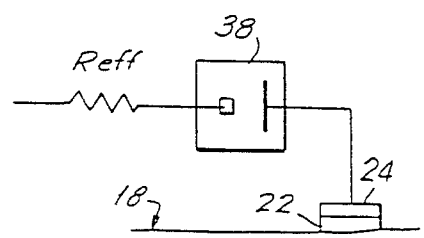
FIG. 4 is an alternate arrangement for the circuit shown in FIG. 3.

Furthermore, as indicated schematically in FIG. 4, applicator 10 may be designed to incorporate provision to insure that the deposit of medicament will cease after a given period of time or after a certain quantity of drug is administered. This can be accomplished by inserting in the circuit an integrating device such as a reverse plating cell 38. Cell 38, as is known in the art, comprises a pair of electrodes on which one is a coating of material to be transferred to the other electrode. When all of the plating material is deposited, after a predetermined period of time based upon the thickness of the original coating has lapsed, or integrated current flow representing the desired quantity of drug to be delivered, there is a large increase in internal resistance resulting in a substantial drop of current flow and an effective halt to drug migration. Such a device can be employed to establish in advance the period of time over which the medicament is to be applied or, as noted above, the quantity of the drug to be delivered. Cell 38 is a relatively high resistance device and could provide for much of the high resistance required for the operation of applicator 10.

Cell 38 may be made a part of contact 32 or be inserted between contact 32 and cover material 14. In addition, provision may be made for current flow to be built up gradually to avoid any shock to the recipient of the drug.

Applicator 10 may be prepared in advance, in different sizes and shapes, sealed within a plastic pouch, with a protective strip over its exposed side. Different drugs can be incorporated for particular applications, batteries may be varied to meet specific current flow requirements, and of course the electrical orientation of each battery would depend on the particular medicament. In the use of the device, the protective strip is removed and the applicator placed on the skin where desired and current flow starts immediately along with migration of the drug.

FIGS. 1–4 hereof show aspects of earlier developments of my invention fully described in earlier filed patent applications, as well as herein. It is specifically understood that I am hereby expressly incorporating into this specification by reference all of the disclosure contained in my earlier filed applications, Ser. No. 660,192 filed Oct. 12, 1984, and PCT/US8500080, filed Jan. 17, 1983. Both said applications are additionally made a part of this instant U.S. patent application by copies attached hereto as pages R1 through R-53, as a matter of convenience.

With the drug applicators and electrode constructions of the present invention, at least two drugs can be transdermally transported simultaneously, across the skin, using one or more transfer modalities. Such an arrangement may be particularly effective in situations where two or more drugs work better together than if taken spearately. For example, aspirin and codeine exhibit a synergistic or improved effect when used together, rather than independently of each other. Other well known drug combinations, such as Dristan exhibit similar results. Thus, with the applicators of the present invention, drug delivery can be varied and may be effected by one or more mass transfer phenomena, such as electroosmosis and iontophoresis and electrophoresis.

It should be recognized that both mass transfer processes require an electric power source, and in the case of electrophoresis an ionized drug migrates from the applicator patch through the skin and into the blood stream, whereas in the case of electroosmosis, a fluid carrier, such as water is likewise transported across the skin and into the blood stream carrying along with it any and all dissolved constituents (ionized drugs or otherwise). Either or both of these two physicochemical phenomena may jointly work together or independently in transdermally carrying a drug or drugs across the skin in a desired dosage release and/or relatively steady pattern.

It should also be noted that as a convenience like numerals are representative of similar elements common to the various embodiments of the invention.

Figure 5:
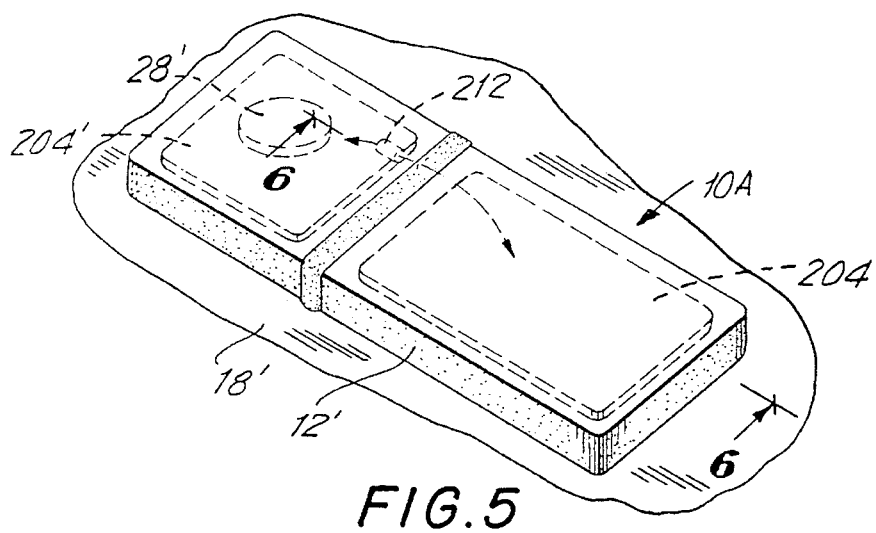
FIG. 5 is a perspective view taken from above or the top of an alternate drug applicator embodying spaced apart electrodes in a side by side fashion.
Figure 6:
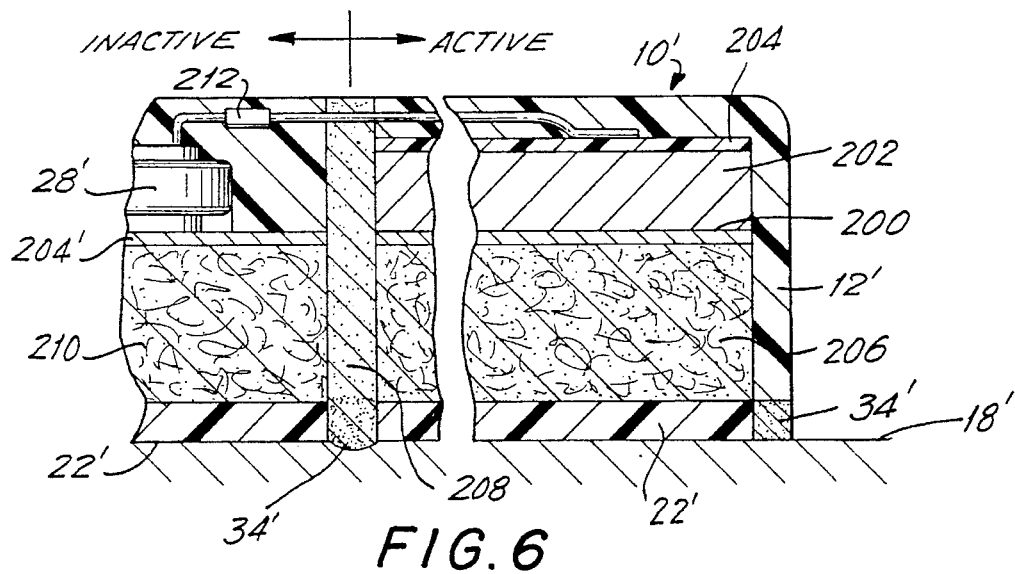
FIG. 6 is a partial cross-sectional view taken along the line 6—6 of FIG. 5.

Referring now to FIGS. 5–6, a side by side patch or applicator 10A construction is illustrated affixed to the skin 18'. As shown therein, element 10' represents the active electrode and it is spaced apart or separated from the inactive electrode by a suitable gap or space, including an air gap. As best shown in FIG. 6, the gap is suitably illustrated as a "dam" 208 which may be made of an inpervious, non-conductive material, such as silicone. This dam 208 maintains electrode separation and provides a seal against the skin so as to preclude any "shorting" effect across the electrodes which might occur due to sweat and other moisture accumulated on the surface of the skin beneath or adjacent to such dam or electrode barrier means. Element 12' is a cover material similar to that outer cover 12 of FIGS. 1–2, although it need not be electrically conductive, since the power source or battery 28' and series connected constant current device 212 (which may suitably comprise a diode) is suitably connected by wire leads or conductors to the separate conductive terminals or film elements 204 and 205'. Preferred elements may be made of a carbonized plastic, foil or other conductive film, such as a metalized mylar.

Membrane 22' is optional as is element 22 of FIGS. 1–4 and comprises a semi-permeable, microporous membrane element having an adhesive and preferably gel-like quality.

Element 34' is a suitable impermeable, insulating material which is preferably formed so as to protrude beyond element 22' and thus form an effective dam-like seal between the separated electrodes forming the applicator patch. Thus, element 34' should be impervious to not only the drugs, water, etc., but it should also be non-conducting.

The "indifferent" electrode 210 which may also comprise a drug matrix or reservoir is disposed between microporous membrane 22' and the conductive element 204'. On the "active" electrode side of the applicator patch 10A, there is disposed suitable drug matrix or reservoir 206, such as an electrolyte solution of low concentration between the nonporous membrane 22' and preferably another semi-permeable membrane 200, so as to provide for a further (upper) high concentration drug matrix or reservoir 202. Such an arrangement for the "active" electrode side of the patch facilitates maintaining a predetermined gradient concentration and desired pH which all aid in providing optimum drug administration.

Figure 7:
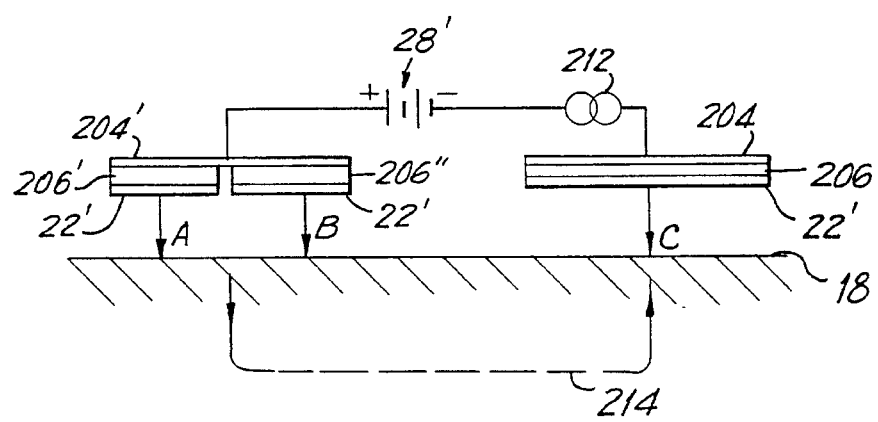
FIG. 7 is a further electrical schematic illustrative of a circuit embodying three active electrodes, such as the active electrode construction exhibited in FIG. 6.

In FIG. 7, which represents an electrical schematic of the invention, numeral 214 (shown in phantom) is current flow generated by the power source or battery 28'. Additionally, this figure illustrates schematically an even further applicator construction or modification comprising three distinct electrodes, all of which are "active" electrodes of similar internal construction, and they are identified by numerals 206, 206' and 206". Reference arrow A, for example, may be employed to transdermally deliver a drug by means of electroosmosis, whereas reference arrows B and C may be employed to deliver transdermally positive ions and negative ions, respectively, by means of iontophoresis or electrophoresis.

It should also be appreciated that electroosmosis moves fluid away from the positive to the negative electrode and such mass transfer process is not very dependent upon concentration levels of the drug. On the other hand, electrophoresis takes place at either the positive or negative electrodes and generally requires a low concentration and high dilution as well as a controlled pH.

Accordingly, as noted hereinabove, although FIGS. 5–6 show different electrode constructions, both sides can be of similar construction, and thus both sides would then comprise "active" electrodes in contrast to, as shown, where the left side being an inactive electrode and the right side being an active electrode. With such applicator constructions, it will be appreciated that one or both halves could deliver iontophoretic drugs or one side of the patch could delivery a drug iontophoretically and the other patch side could deliver a drug electroosmotically.

It should be noted, and as is clearly illustrated in FIG. 5, the electrodes need not necessarily be of the same size (or even shape) although they may be conveniently manufactured to the same size and/or configuration. In a like manner, it will be recognized that these electrodes and applicator constructions in effect do not really incorporate a true "lip" area or skin electrode as does the device of FIGS. 1–4, although the element 34' still serves as a tacky sealing boundry about the periphery of the applicator, as does element 34 of FIG. 2.

Figure 8:
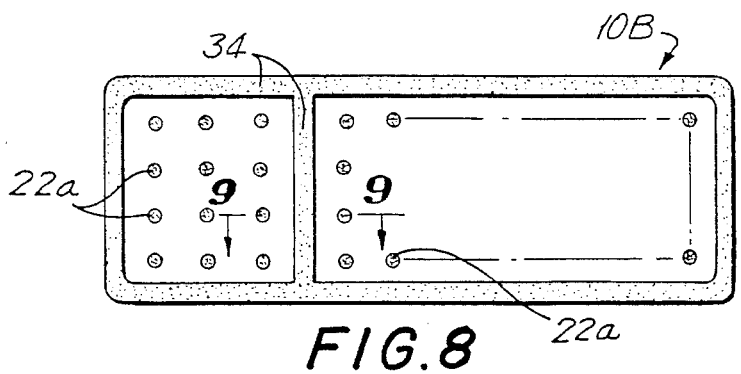
FIG. 8 is a bottom plan view of yet another drug applicator structure incorporating a plurality of high tack spots across the electrodes employed and the drug reservoir or matrix.
Figure 9:
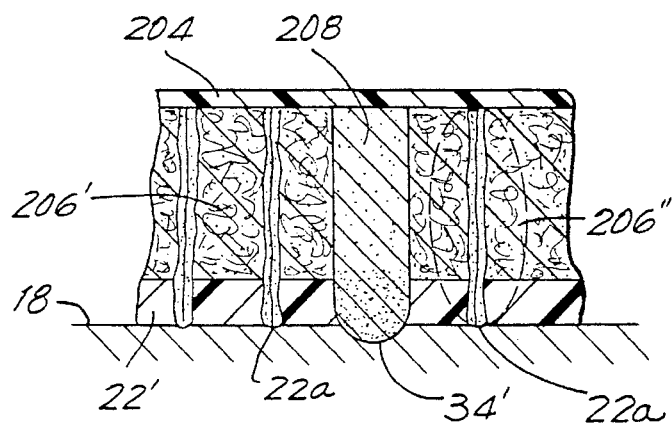
FIG. 9 is a partial cross-sectional view taken along the line 9—9 of FIG. 8.

In FIGS. 8–9, there is shown an alternate construction of yet another suitably unequally sized, electrode configurations, wherein the applicator 10B includes a plurality of randomly placed or preferably uniformly aligned rows of a high tack, impermeable gel 22a. Such an adhesive gel aids in retaining the patch on one's skin and inasmuch as some areas of the patch would thus be more tacky than other areas of the patch, such construction enables the manufacture of a patch wherein the adhesive gel 22' has less adhesive strength than that of the gel 22a. By this arrangement, the patch may be easily removed from the skin and replaced thereon should one require removal and replacement of the same patch, say for example, upon bathing or showering, or even pursuant to a physician's instructions where it is desired to transmit a drug dosage periodically in lieu of a continuous steady state condition.

As best shown in FIG. 9, the drug matrixes or reservoirs of the electrodes are represented by reference numerals 206' and 206", and same are separated by a suitable silicone barrier dam 208. The high tack zones or areas 22a are generally of a harder gel than that gel of 22'. Thus, these elements 22a which may be either of elongated fiber-like construction or of stubby spherical shape (not shown in phantom) they both serve the same identical purpose. However, as one construction may be easier or less expensive to fabricate than the other, neither one is more preferable than the other and both are considered within the scope of my invention.

Figure 10:
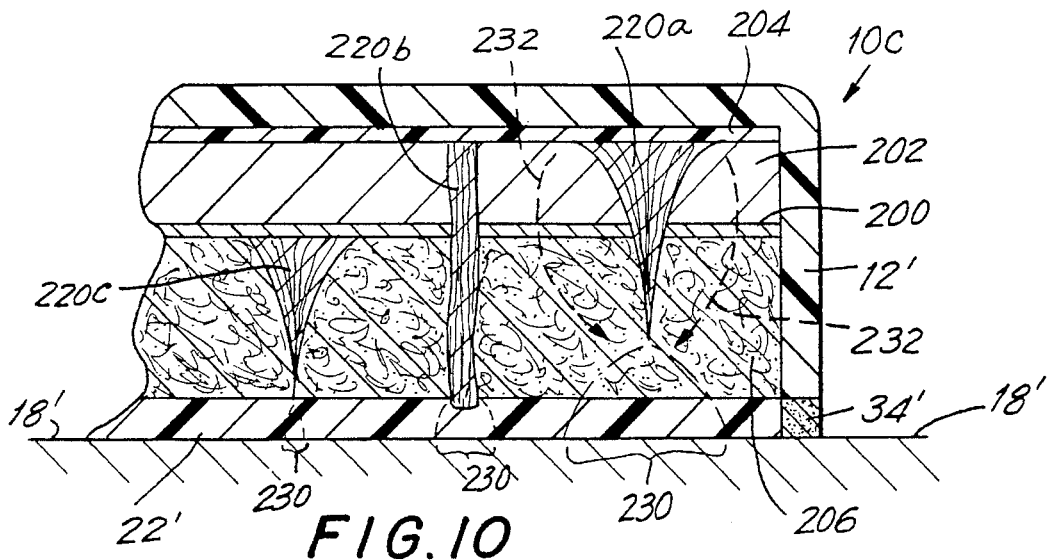
FIG. 10 is a partial, cross-sectional view of a further alternate electrode construction.
Figure 11:
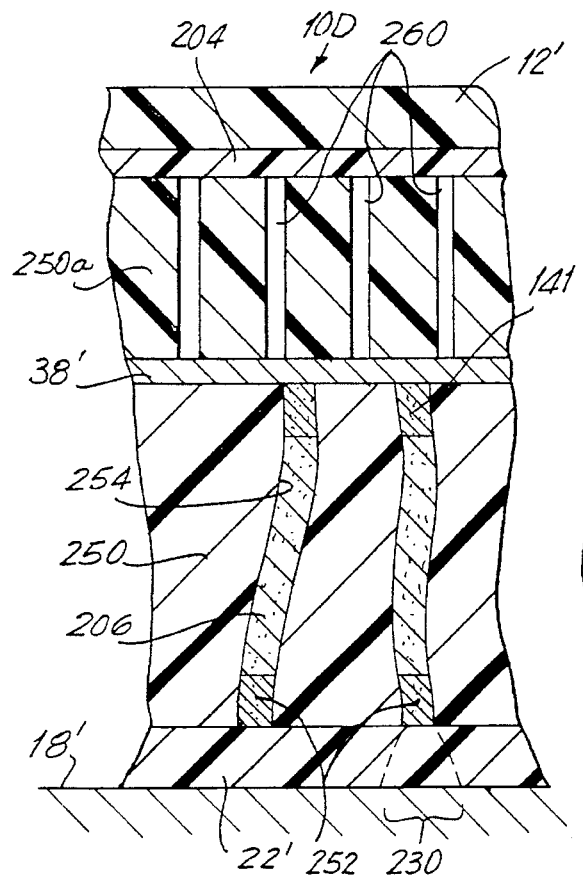
FIG. 11 is another partial, cross-sectional view of yet a further electrode modification.
Figure 12:
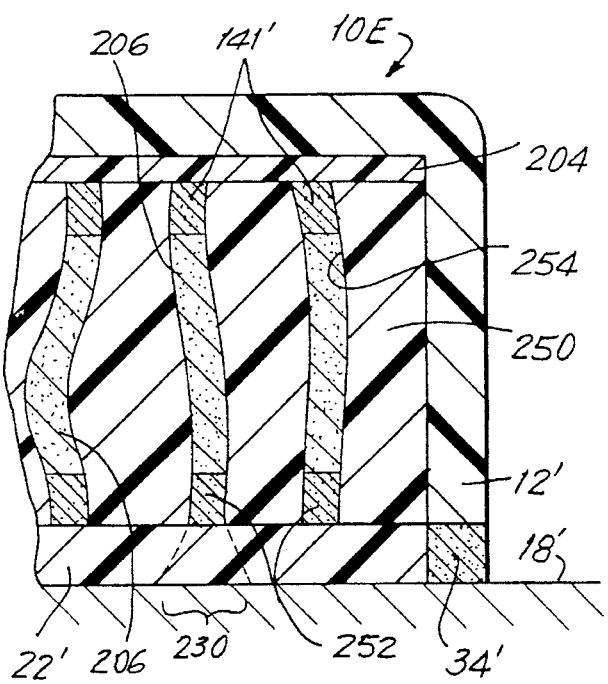
FIG. 12 is yet another partial, cross-sectional view of yet another alternate electrode structure.

Other electrode structures, suitable for use in making applicators of the invention include those electrodes shown in FIGS. 10–12, respectively as 10C, 10D and 10E. As illustrated in FIG. 10, a plurality of conductive fiber-like elements 220a, 220b, and 220c transverse either or both drug matrix or reservoir 202,206. These fibers may suitably comprise carbon and/or graphite or other elements, such as conductive plastic containing carbon. The conductive fibers reinforce the applicator or patch construction in a manner similar to the elements 22a contained in the electrodes of FIGS. 8 and 9. The primary purpose of such fiber structures is to bring the current flow more directly to the zone where the electrically induced mass transfer phenomena and drug delivery takes place. This is represented by the zone 230 and the reference arrows 232 (shown in phantom) illustrate in general the concentration gradient. Thus, as the area or zone 230 is depleted of drug, as a result of the mass transfer phenomena, this induces the drug to migrate from or out of the high concentration zone 202 to the depleted area or zone, as is best exemplified by the reference arrows 232. The transport speed is generally determined by the interaction of the drug and the media. This thus enables the patch to maintain low electrical mass transfer in zone 230, and it limits or or minimizes the amount of time the drug is exposed to the electrical forces. Therefore, most of the drug in the reservoir is not subjected to current as the mass transfer phenomena takes place only in the vicinity of zone 230. Clearly, the fibers are prevented from extending transversely across the full height or depth of the electrode or patch construction as to do so would cause a short out at the skin and thus would cause an undesirable sensation. Also, the shapes of the fibers may suitably be varied or of the same configuration, such as elongated (220b) or tapering (220a and 220c). In addition, the fibers may extend from element 204 to the reservoir 206 or element 22', or they may extend from element 200 to element 22'. Additionally, it will be appreciated that tack spots and/or the conductive fibers permit drug delivery from small patch areas and the osmotically replenishing of the drug as it migrates through the skin.

As best shown in FIG. 11, a plurality of micro-tubes (or holes) 254 are suitably randomly provided in a non-conductive, plastic-like inert area 250 (not unlike a sponge with a multiplicity of voids and passageways generally oriented in a vertical direction although not necessarily in straight lines). The tubes 254 may optimally be provided at their ends with the plugs 141 and 252.

Plug 252, for example, may form an ion-permeable gel which may take the form of an ion-selective retention gel. Alternatively, plug 252 could also be a selective barrier against air, oxygen and other contaminants. The plug 252 may also suitably contain appropriate buffers and/or enhancers or any other compounds which desirably are to be transmitted initially transdermally, such as a skin permeability enhancer. Such a plug arrangement, can facilitate a quick, fast acting dosage so as to provide for an immediate blood serum drug level dosage. Such a high rate of delivery is in contrast to a more normalized delivery rate of a transdermal drug electrically transported without the aid of any enhancers or the like.

Alternatively, conductive (such as carbon containing) fibers 260 embedded in a suitably inert material 250a may be provided between element 204 and a suitably reverse plating cell 38'. The reverse plating cell 38' enables a different drug delivery sequence and/or enables one to provide for different delivery rates of drugs. The inert material 250a with its transverse fibers 260 can only conduct electricity in a direction perpendicular to its surface, and the individual fiber's resistance have an electrical current limiting effect. Thus, such an arrangement provides a so called "fail safe" mode of delivering current to the skin, i.e. the current density at the skin surface cannot increase above the "feel" threshold should the applicator patch become loose during use. Note that all of the drugs 206 to be transported reside within the tubes 254.

FIG. 12 represents an embodiment of an electrode for an applicator similar to that of FIG. 11, but without the conductive fibers 260, inert mass 250a, and reverse plating cell 38'. Here, plug 141' is of a suitably electrically resistive material as is the plug 141' of FIG. 11.

It will also be apparent that there are many more fibers 260 than tubes 254, and both fibers and tubes are randomly disposed. The conductive fibers 260 have a function similar to that of the electrically resistive material 141, 141'.

In a series of tests conducted using applicators made generally in accordance with that design exemplified by the "inactive" electrode shown in FIG. 6, using drugs such as testosterone, tobramycin, and aspirin, the following tabled results were obtained from sampled blood and urine of rabbits which formed the test animals in all cases. The control represented patches or applicators without any power source, but containing drug. Note that the first two drugs were radiotagged, whereas aspirin was tested both as radiotagged and conventional or untagged, and the samples taken were assayed for the total radioactive count.

Albino rabbits were employed for the tests, and each rabbit weighed at least six pounds. (Note: rabbits do not have sebaceous glands). The back of each rabbit's neck was shaved to permit better contact of the applicators and the skin or epidermis. The applicators were secured in place by an elastic bandage.

Each applicator was of the same size (3"×4") and equally divided, with one half being the cathodic or negatively charged electrode, and the other half being the anode or positively charged electrode; and the target drug was loaded equally into both halves of the applicator. Only one drug was employed in each test. The target drug was also dissolved in distilled water and 4 ml of the resultant solution was loaded into the patches.

The blood samples were secured prior to initiation of drug delivery, and at hourly intervals for the next six hours. The urine samples were occasionally collected to determine if the drug was being metabolized and eliminated from the animals during the course of the experiments. Where more than one series of tests were employed using the same groups of animals, at least 36 hours elapsed between the end of one test series and the beginning of a second test in order to insure that there was no interference between each test series. In one series of tests, the patches were without electrical power, and in another series of tests, the patches were powered by table top power supplies for purposes of convenience and expediency.

TABLE I

Testosterone Drug Delivery
The control series, with no applied power, did not yield
any levels of radioactivity in the sampled blood. When the
table top battery supply was connected to the patch,
the following results were obtained

| TIME | Counts per minute | |
|---|---|---|
| | Powered Patch | Unpowered Patch |
| 0 h | 0 | 0 |
| 1 h | 32 | 0 |
| 2 h | 67 | 0 |
| 3 h | 71 | 0 |
| 4 h | 78 | 0 |
| 5 h | 81 | 0 |
| 6 h | 88 | 0 | n = rabbits
6 series of tests

The urine was collected into two batches. The first three hours of pooled urine per animal exhibited no radioactivity (less than one count per minute). The second three hours average radioactivity was 7 dpm.

TABLE II

Trobramycin Drug Delivery
There was no noticeable transdermal delivery of trobramycin witout applied power. The results over the six hours of testing ranged from 0 to 2 disintegrations per minute. When the table top power supply was applied to the patch, the results were noticeably different, as is seen hereinbelow.

| TIME | Counts per minute | |
|---|---|---|
| | Powered Patch | Unpowered Patch |
| 0 h | 0.2 | 0.1 |
| 1 h | 10 | 0 |
| 2 h | 19 | 0.5 |
| 3 h | 27 | 0.1 |
| 4 h | 35 | 0.2 |
| 6 h | 40 | 0.2 | n = 9 rabbits
2 test series

The urine samples demonstrated no radioactivity during the first three hours. The average radioactivity in the subsequent period was 2.5 dpm.

TABLE III

Aspirin Drug Delivery
As radioactively tagged aspirin was not obtainable,
thus liquid aspirin was employed and assayed using conventional
methods. The results for the powered delivery were as follows.

| TIME | Aspirin Level |
|---|---|
| 0 h | 0 |
| 2 h | 5 |
| 4 h | 23 |
| 6 h | 57 | n = 14 rabbits
2 test series

It is clear from these tests that due to the migration phenomenon drugs can be transported transdermally using an electrically powered applicator, and that desired drug levels may be obtained by environmental optimization, i.e. pH, drug loading, current density, etc.

It will also be appreciated that since both ionic and non-ionic drugs can be transdermally delivered, it may not be necessary to ionically charge a non-ionic drug, should it be desired to transdermally transport such a drug by an electrically powered applicator patch.

Also, the applicators may be made with the same electrode configurations or with different designs, such as those constructions described herein. It is also within the scope of the present invention to have an applicator patch embodying three different electrode structures, such as that described with reference to FIG. 7. Furthermore, although both an active and an inactive electrode are required for use with an electrophoresis mass transfer drug system, all of the electrodes may be active in those systems employed where either electroosmosis or both electroosmosis and electrophoretic systems are utilized to deliver one or more drugs into the blood stream.

Although the present invention has been described in some detail by way of illustration and example for purposes of clarity and understanding, it will, of course, be understood that various changes and modifications may be made in the form, details, and arrangements of the parts without departing from the scope of the invention as set forth in the following claims.

What is claimed:

1. An electrically powered transdermal drug applicator having at least one medicament for application to a living body for the migration of the at least one medicament through the skin into the blood stream comprising essentially of the following elements:

Three generally flat electrode elements, free of a flexible, non-conductive substrate having conductive coated areas and free of any folds, and forming a transdermal drug applicator with multiple electrode elements, and with one electrode element thereof being separated from the other two which are juxtaposed to each other, and with two of said three electrode elements being either an active medicament containing electrode element or an inactive electrode element having no medicament, reservoir means having a predetermined depth and a plurality of sides forming a periphery, in each of said electrode elements of said transdermal drug applicator, with at least one of said juxtaposed electrode elements including said reservoir means containing said at least one medicament; and said reservoir means being free of transversing elements passing through at least a portion of said electrode elements and/or said reservoir means;

each of said electrode elements, including said at least one having said at least one medicament in said reservoir means having an impermeable tacky, non-conducting and insulating barrier seal coextensive with the sides of said electrode elements and said reservoir means and extending along at least the full depth of said electrode elements and said reservoir means, so as to form an effective dam between said juxtaposed electrode elements and said reservoir means, with an end lip-like curtain about all sides forming said periphery of said electrode elements and said reservoir means; the dam-like barrier seal maintaining electrode and reservoir separation of said juxtaposed electrode and reservoir elements from each other and forming a tacky peripheral lip seal against the skin for precluding electrical shorting across said electrode-reservoir elements;

an electrical circuit, including a power source and current control device, for supplying electrical power in parallel to all of said electrode elements and said reservoir means and forming a closed electrical loop circuit from said power source connected via conductors to said electrode elements and said reservoir means, and the skin when the transdermal drug applicator is applied thereto;

a relatively, thin non-conductive cover means partially enclosing and conforming to said electrode elements and said reservoir means so as to envelope at least said electrode elements and said reservoir means and at least portions of said electrical circuit and leaving sides of said electrode elements and said reservoir means exposed for contact with the skin, and adhesive means for affixing said transdermal drug applicator to said skin, whereby said electrical circuit through the skin is formed when said transdermal drug applicator is adhesively affixed to said skin, thereby creating at least one physico/chemical mass transfer phenomenon which causes said at least one medicament to migrate from said reservoir means containing said at least one medicament through the skin and into the blood stream of said living body.

2. A transdermal drug applicator according to claim 1, wherein at least one of said electrode elements constitutes an inactive or indifferent electrode.

3. A transdermal drug applicator according to claim 1, wherein all of said electrode elements are active electrodes.

4. A transdermal drug applicator according to claim 1, wherein said reservoir means contain different drugs.

5. The transdermal drug applicator according to claim 1, wherein at least one electrode element is separated from said other electrode elements by a gap.

6. The transdermal drug applicator according to claim 5, wherein said gap is an air gap.

7. The transdermal drug applicator according to claim 1, wherein said barrier seal dam is made of an impervious, non-conducting material.

8. The transdermal drug applicator according to claim 7, wherein said impervious, non-conducting material is silicone.

9. A transdermal drug applicator according to claim 1, wherein each said electrode element comprises a conductive element adjacent its respective reservoir means; and said electrical circuit being connected to said conductive elements for driving each reservoir means so as to enable said at least one physico/chemical mass transfer phenomenon to take place at the surface of said skin.

10. An electrically powered transdermal drug applicator having at least one medicament for application to a living body for the migration of the at least one medicament through the skin into the blood stream comprising:

Three generally flat electrode elements, free of a flexible, non-conductive substrate having conductive coated areas and free of any folds, and forming a transdermal drug applicator with multiple electrode elements, and with one electrode element thereof being separated from the other two which are juxtaposed to each other, and with two of said three electrode elements being either an active medicament containing electrode element or an inactive electrode element having no medicament, reservoir means having a predetermined depth and a plurality of sides forming a periphery, in each of said electrode elements of said transdermal drug applicator, with at least one of said juxtaposed electrode elements including said reservoir means containing said at least one medicament; and said reservoir means being free of transversing elements passing through at least a portion of said electrode elements and/or said reservoir means;

each of said electrode elements, including said at least one having said at least one medicament in said reservoir means having an impermeable tacky, non-conducting and insulating barrier seal coextensive with the sides of said electrode elements and said reservoir means and extending along at least the full depth of said electrode elements and said reservoir means, so as to form an effective dam between said juxtaposed electrode elements and said reservoir means, with an end lip-like curtain about all sides forming said periphery of said electrode elements and said reservoir means; the dam-like barrier seal maintaining electrode and reservoir separation of said juxtaposed electrode and reservoir elements from said other and forming a tacky peripheral lip seal against the skin for precluding electrical shorting across said electrode-reservoir elements;

an electrical circuit, including a power source and current control device, for supplying electrical power in parallel to all of said electrode elements and said reservoir means and forming a closed electrical loop circuit from said power source connected via conductors to said electrode elements and said reservoir means, and the skin when the transdermal drug applicator is applied thereto;

a relatively thin non-conductive cover means partially enclosing and conforming to said electrode elemnts and said reservoir means so as to envelope at least said electrode elements and said reservoir means and at least portions of said electrical circuit and leaving sides of said electrode elements and said reservoir means exposed for contact with the skin, and adhesive means for affixing said transdermal drug applicator to said skin, whereby said electrical circuit through the skin is formed when said transdermal drug applicator is adhesively affixed to said skin, therby creating at least one physico/chemical mass transfer phenomenon which causes said at least one medicament to migrate from said reservoir means containing said at least one medicament through the skin and into the blood stream of said living body; and wherein said at least one electrode element including said reservoir means containing said at least one medicament including high and low drug concentration zones separated by a membrane forming a drug gradient across said reservoir means.

11. A transdermal drug applicator according to claim 10, wherein said electrode elements are generally of the same construction.

12. A transdermal drug applicator according to claim 10, wherein said electrode elements are of different constructions.

13. A transdermal drug applicator according to claim 10, wherein said electrode elements are of different size.

14. The transdermal drug applicator according to claim 10, wherein said membrane is a semi-permeable member for maintaining a predetermined drug gradient concentration and desired pH of said reservoir means, whereby optimum administration of the delivery of said at least one medicament is achieved.

* * * * *